United States Patent [19]

Dremel et al.

[11] Patent Number: 5,223,224
[45] Date of Patent: Jun. 29, 1993

[54] SENSOR ARRANGEMENT FOR FLOW INJECTION ANALYSIS

[75] Inventors: Bernd A. Dremel; Detlef H. Hanisch, both of Brunswick, Fed. Rep. of Germany

[73] Assignee: Gesellschaft fur Biotechnologische Forschung mbH (GBF), Brunswick, Fed. Rep. of Germany

[21] Appl. No.: 625,840

[22] Filed: Dec. 11, 1990

[30] Foreign Application Priority Data

Dec. 13, 1989 [DE] Fed. Rep. of Germany ........ 3941162

[51] Int. Cl.$^5$ .......................................... G01N 21/00
[52] U.S. Cl. .......................................... 422/81; 422/62; 422/82.06; 422/82.07; 436/55; 435/288; 356/244; 356/440
[58] Field of Search ............. 422/81, 82.06, 82.07, 422/55, 58, 62; 356/440, 244; 436/55; 435/288, 289, 291, 808

[56] References Cited

U.S. PATENT DOCUMENTS

| | | | |
|---|---|---|---|
| 4,424,559 | 1/1984 | Lorincz et al. | 422/62 X |
| 4,443,407 | 4/1984 | Weinberg et al. | 422/81 X |
| 4,726,929 | 2/1988 | Gropper et al. | 422/82 X |
| 4,786,394 | 11/1988 | Enzer et al. | 422/81 X |
| 4,997,627 | 3/1991 | Bergkuist et al. | 435/289 X |
| 5,037,737 | 8/1991 | Liffmann et al. | 435/288 X |
| 5,045,282 | 9/1991 | Kritzman et al. | 422/82.07 X |

Primary Examiner—Lynn M. Kummert
Attorney, Agent, or Firm—Kane, Dalsimer, Sullivan, Kurucz, Levy, Eisele and Richard

[57] ABSTRACT

A sensor arrangement for flow injection analysis, includes an enzyme reactor and a chemical/physical sensor. The sensor arrangement is designed as a sealed module and a flow channel of great length is accommodated in the module. By this sensor arrangement, gases generated or consumed in the enzyme reactor are detected without interfering gas exchange with the environment.

11 Claims, 7 Drawing Sheets

SENSOR ARRANGEMENT FOR FLOW INJECTION ANALYSIS

BACKGROUND OF THE INVENTION

1. Field of the Invention

The invention relates to a sensor arrangement for flow injection analysis, comprising an enzyme reactor and a chemical/physical sensor. Enzyme reactor is here understood to mean all immobilised biological components, such as enzymes, antibodies or the like, which can ensure a particular substrate specificity.

2. Brief Description of Related Art

Flow injection analysis (FIA) is a wet-chemical analysis procedure which in recent years has developed to become a valuable and frequently used method. In flow injection analysis, the sample to be analysed is injected into a stream of an appropriate liquid (carrier liquid) and is conveyed together with this liquid to a detection system. In the detection system the passage of the sample is established and the analyte content of the sample is quantitatively determined in an evaluation device from the output signal. Although flow injection analysis is not a continuous analysis procedure, the repetition rate of the individual measurements is nevertheless generally so high that in many cases of application the procedure can be regarded as being quasi-continuous.

Flow injection analysis thus makes it possible to transfer conventional analytical laboratory techniques to a continuous flow process. It is possible to carry out fully automatic pipetting, diluting and mixing processes as well as chemical reactions or measurements by means of electrodes or optodes.

Suitable detectors are any devices which convert the chemical detection reaction quantitatively into an electrical signal. Examples of detectors are chemical/physical sensors and transducers such as photometers, fluorometers, refractometers, luminescence detectors, turbidimeters, pH- and ion-sensitive electrodes, voltametric and amperometric detectors, conductimeters, thermistors, semiconductor structures (FETs) etc.

One precondition for an error-free analysis is that there should be no air bubbles present in the liquid stream, since this frequently results in completely false analysis results. The injection volume is reduced, leading to mixing and reaction errors and to measurement errors in the detection system. Measures for preventing or eliminating air bubbles in flow injection systems consist in degasing the liquids used, which is relatively expensive and not without risk. A recent proposal for counteracting air bubbles still present in the system involves the use of air bubble traps which catch the air bubbles present in the flow system and convey them onwards.

Nor is flow injection analysis restricted to wet-chemical determination. By using enzymes in dissolved or immobilised form, immobilised antigens/antibodies, organelles and microorganisms, the range of application of flow injection analysis can be greatly widened.

The use of enzymes in flow injection analysis permits a specific determination of analytes in complex media too. The enzymes are usually immobilised, i.e. used in an enzyme reactor which permits the determination of enzymatic conversions by the analyte, for example the consumption of educts such as, for example, oxygen and for formation of products such as, for example, carbon dioxide or of acids.

For achieving accurate analysis results, the biological components have hitherto been applied directly to the chemical/physical sensor, and the chemical/physical sensor (transducer) has been combined in one component part. The arrangement is in this case such that the analytes must diffuse through the enzyme layer to the chemical/physical sensor. The considerable spatial proximity prevents the concentration of the analyte, to be determined by the chemical/physical sensor, from rapidly decreasing as a result of dispersion or gas exchange with the environment. However, in order not to alter the response behaviour and the linear measuring range in an undesirable manner, due to the given geometry of the component part only a limited amount of enzyme can be used, i.e. an enzyme layer of specific thickness. As a result of this the sensor arrangement is very sensitive to interference.

Another sensor arrangement for flow injection analysis has been developed in which the biological component is separated from the chemical/physical sensor. This construction is particularly advantageous for biosensors with enzymes of low activity and/or stability. In contrast to the layer arrangement of biological component and transducer, the spatial separation allows a greater amount of enzyme to be used. The enzyme excess thus obtained results in a decrease in the sensitivity of the system in relation to interference ions (e.g. heavy metal ions) and fluctuating pH values. However, one disadvantage of the separation of the biological component from the chemical/physical sensor is that the gases to be determined can escape in the sensor arrangement, so that these gases may be detected only incompletely by the downstream chemical/physical sensor. This occurs in particular at low flow rates.

SUMMARY OF THE INVENTION

The invention is based on the object of providing a sensor arrangement for flow injection analysis, comprising an enzyme reactor and a chemical/physical sensor, in which both are combined in one component part and the use of a sufficiently large amount of enzyme is permitted.

This object is achieved by the invention in a sensor comprising an enzyme reactor and a chemical/physical sensor in a sealed module and having a flow channel of pre-determined length accommodated in the module.

DETAILED DESCRIPTION OF THE PREFERRED EMBODIMENTS OF THE INVENTION

A sensor arrangement according to the invention for flow injection analysis thus comprises an enzyme reactor and a chemical/physical sensor and is designed as one module, in which respect a flow channel of great length is accommodated in the module. With this integrated manner of construction, there is no interfering diffusion of gases such as, for example, oxygen and carbon dioxide through the walls, even if the flow rates are low. There is therefore no interfering gas exchange between gases to be detected and the environment, since the gases generated or consumed in the biosensor remain in the module, which also contains the chemical/physical sensor, as a result of which no detection distortions can arise. The use of a flow channel of great length makes it possible to operate at high flow rates thus reducing to a minimum the disadvantage of air bubbles possibly being formed or being left behind. A further advantage of the module construction consists in that the sensor arrangement can be easily replaced, and likewise the enzyme reactors. In the sensor arrangement according to the invention it is possible to use advantageously a larger amount of enzyme than is the case when the biological component is directly immobilised in a layer arrangement directly on the transducer and in which an enzyme excess can only be obtained to a limited extent since diffusion phenomena can adversely affect the response times and measuring ranges of the sensor. The dimensions of the enzyme reactor according to the invention can be very flexible within certain limits.

A particularly advantageous design of the flow channel consists in its having a meander formation, by means of which an especially large channel length can be provided while saving space. Moreover, interference caused by air bubbles can be reduced, since these bubbles are flushed out by means of the high flow rate.

In the sensor arrangement according to the invention the enzyme reactor is advantageously designed as a replaceable insert cartridge. This permits a simple replacement of the enzyme reactor when required, whereas the longlife chemical/physical sensors such as, for example, oxygen and carbon dioxide optodes, remain in the module. In this way the analysis costs are markedly reduced. A further advantage of this arrangement is that a quick replacement or conversion is possible for the purpose of carrying out another analysis method.

A particularly simple replacement of the insert cartridge can be achieved if the insert cartridge is screwed into the module.

In a preferred exemplary embodiment of the sensor arrangement according to the invention, the housing part of the enzyme reactor is made of plexiglass [poly(-methy)methacrylate] or of clear PVC (polyvinyl chloride). The production costs are favourable.

The module advantageously has a flow chamber containing the flow channel, on which chamber there is clamped a securing device for the chemical/physical sensor. This construction c an be designed so as to be self-sealing, so that no rubber seal is necessary, with the corresponding disadvantages such as, for example, brittleness or twisting. The sealing is achieved by means of the clamping, i.e. the pressing of the securing device of the chemical/physical sensor onto the flow chamber part.

A particularly simple design of the clamped connection consists in an arrangement with union nut and counterscrew.

The chemical/physical sensor preferably comprises a transmitter in contact with the flow channel and emitting optical signals, a transparent window and an optical receiver arrange behind the window. In this arrangement the measurement detection is separate from the measurement conversion, the latter being media-independent as a result of the separation (window).

The optical receiver is advantageously an optical fibre bundle, which can be arranged in a space-saving manner.

The optical window is preferably made of sapphire or quartz.

An advantageous design of the optical transmitter is an optode consisting of a support film and an indicator layer arranged on the latter. This arrangement is highly sensitive and at the same time space-saving.

The support film used is preferably a polyester film based on ethylene glycol and terephthalic acid, i.e. a mylarfilm, the indicator layer preferably being a silicone layer with fluorescence indicator.

A particularly simple construction is afforded with the transmitter and optical window being pressed fluid-tight onto the securing device, in which respect the transmitter has a sealing layer, and an anti-displacement means is provided for the transmitter. In this way, no additional parts are needed, and the assembly is simplified.

The invention will be described in greater detail below with reference to a preferred exemplary embodiment and to the drawings of FIGS. 1–20.

Figure 1:
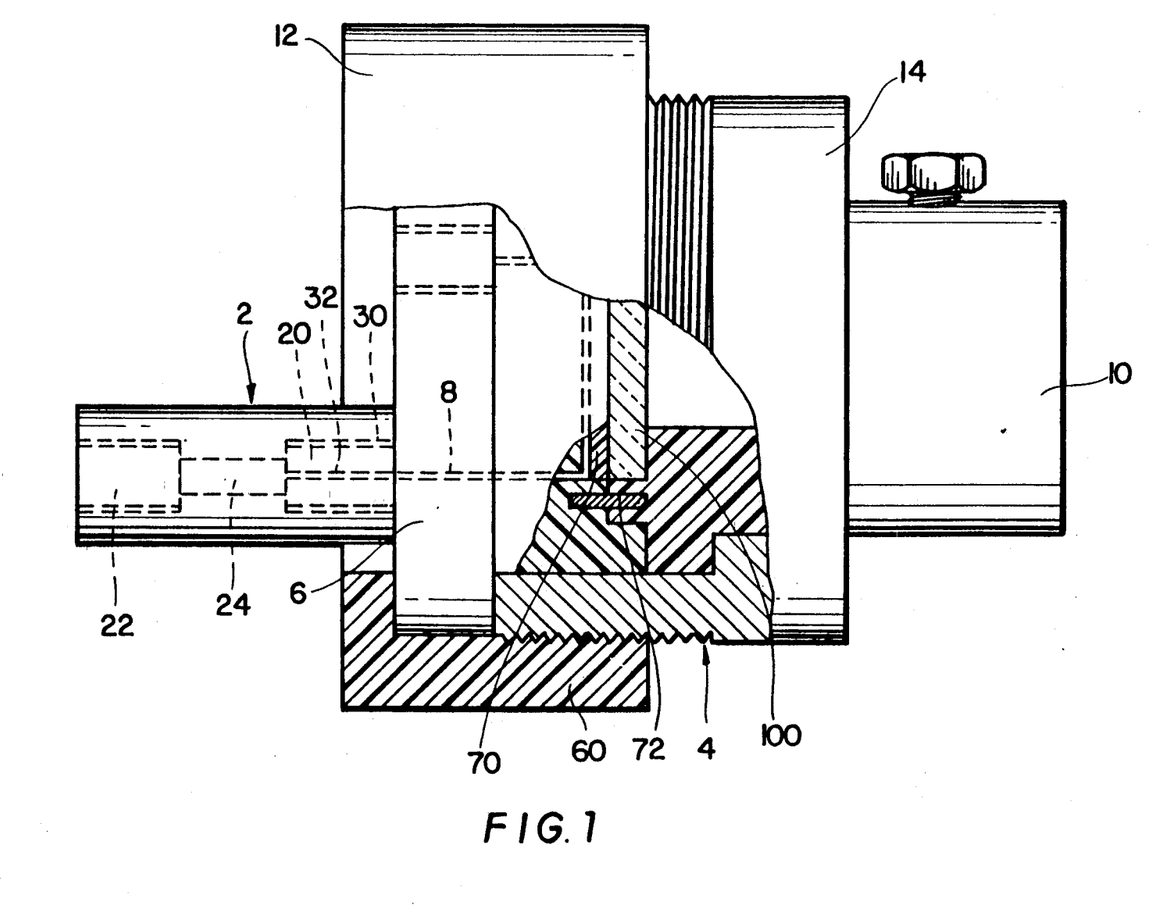
FIG. 1 shows a partially broken view of the sensor arrangement, with biosensor and chemical/physical sensor screwed together.

FIG. 1 shows an exemplary embodiment of the sensor arrangement according to the invention for flow injection analysis. The sensor arrangement generally having a housing made of black PVC (polyvinylchloride) comprises an enzyme reactor 2 and a chemical/physical sensor 4, both of which are in contact with the flow channel 8 contained in a flow chamber 6. The chemical/physical sensor 4 has a securing device 10 which is clamped on the flow chamber 6 by means of a union nut 12 and a counter-screw 14 made of VA steel.

The enzyme reactor 2 comprises central bores 20, 22 and a central receiving cylinder 24 connecting these. The enzyme reactor 2 is screwed directly by means of the bore 20 onto an externally threaded support 30 of the flow chamber 6, which has a central bore 32 as end section of the flow channel 8. The actual assembly of the biological component is accommodate in the receiving cylinder 24 of the enzyme reactor 2. The bore 22 is intended for the connection and guiding through of measurement lines, for example a light-conducting single fibre or the like.

Figure 2:
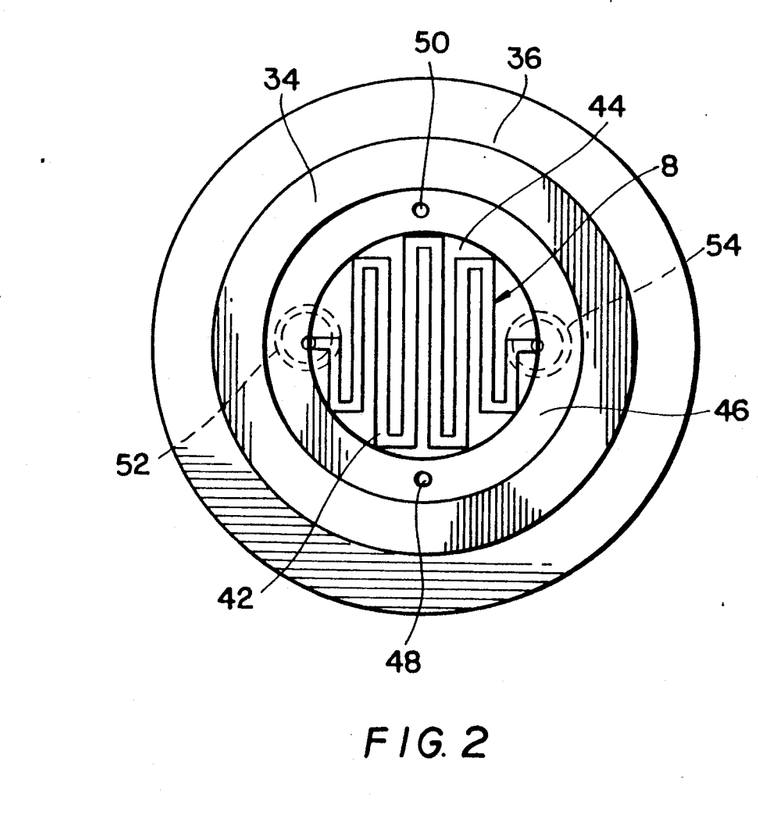
FIG. 2 shows a front view of the flow chamber forming part of the sensor arrangement in FIG. 1 and containing the flow channel, in which respect the enzyme reactor and securing parts are omitted.
Figure 3:
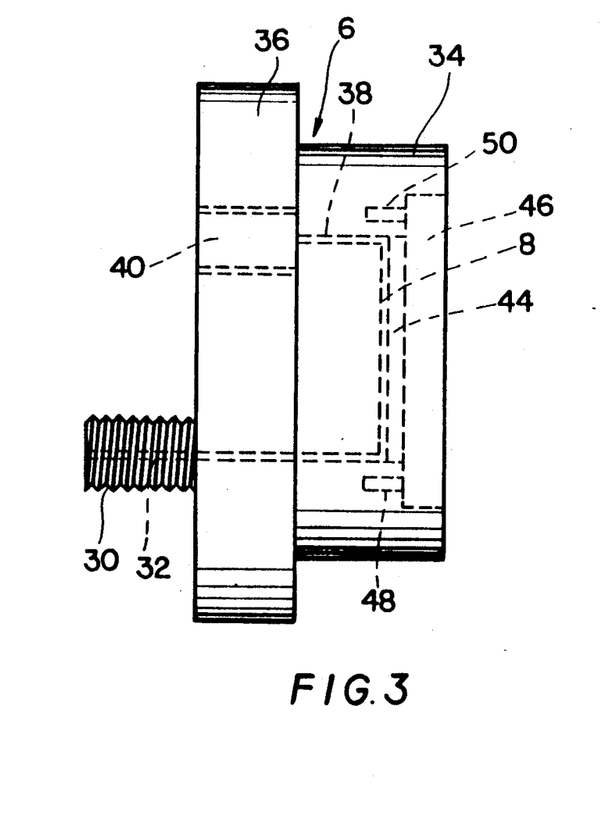
FIG. 3 is a side view of the part shown in FIG. 2.

The flow chamber 6 is shown in greater detail and in FIG. 2 and FIG. 3. It comprises a cylindrical chamber 34 and a flange 36 which bears the support 30 on the outside, the bore 32 of the support 30 continuing through the flange 36 and the chamber 34 as far as an optode 70 (not shown in FIG. 2) still to be described. Opposite the bore 32, the chamber 34 has another bore 38 which merges into a larger bore 40 in the flange 36. The bores 32, 38 ending at the level of the optode 70 are connected to one another by means of a meandering channel 42. Adjacent to the meandering channel, the chamber 34 has a cylindrical recess 44 having a diameter corresponding approximately to the distance of the bores 32 and 38 from one another. The recess 44 is intended to receive the optode 70. The recess 44 widens into a further cylindrical recess 46 with a greater diameter, provided on its base with two axially directed bores 48, 50 for receiving fixing pins 72 to be described hereinbelow. Inlet and outlet bores 52, 54 as connections for the flow channel B are only shown diagrammatically in FIG. 2 and FIG. 3.

Figure 4:
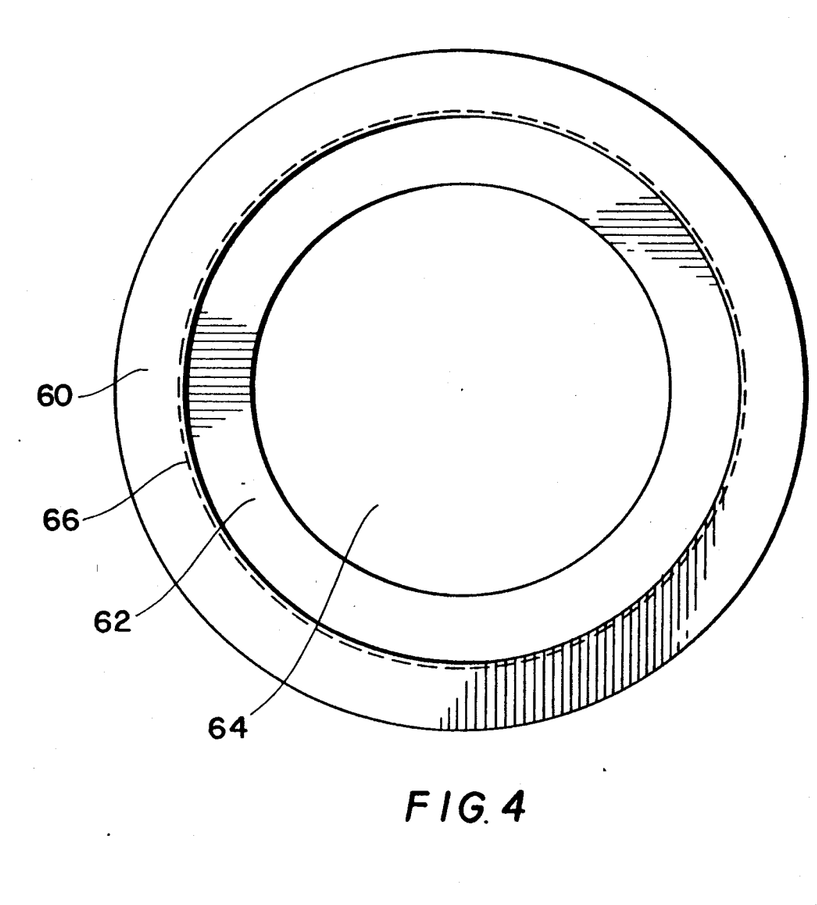
FIG. 4 shows a front view of the union nut and counter-screw.
Figure 5:
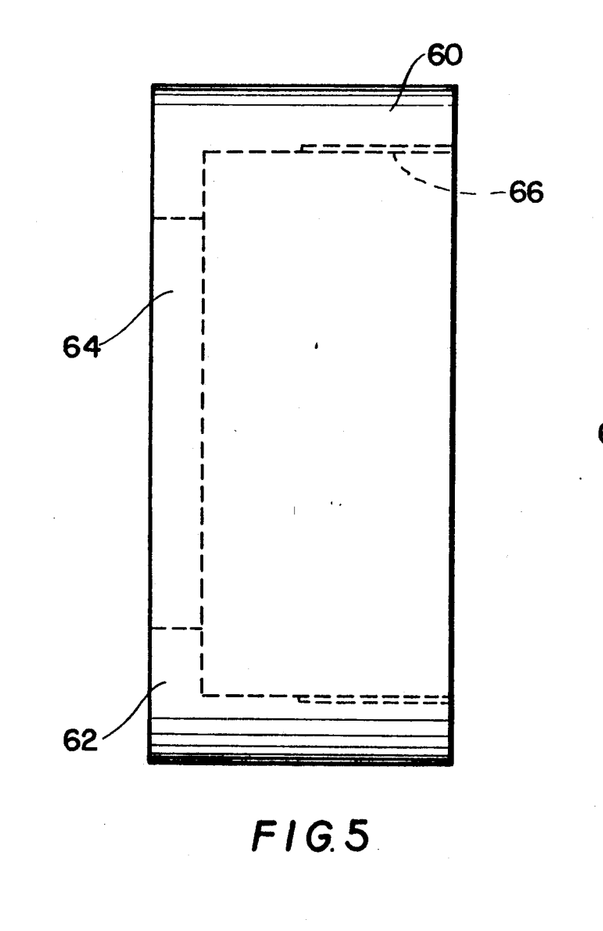
FIG. 5 shows a side view of the union nut and counter-screw.

FIG. 4 and FIG. 5 shows the union nut 12 in a front view and side view. The union nut comprises a cylindrical annular body 60 with a plane base 62, which has a central opening 64. On the inside the annular body 60 has a thread 66 by means of which the union nut 12 and the counter-screw 14 are screwed to one another.

Figure 6:
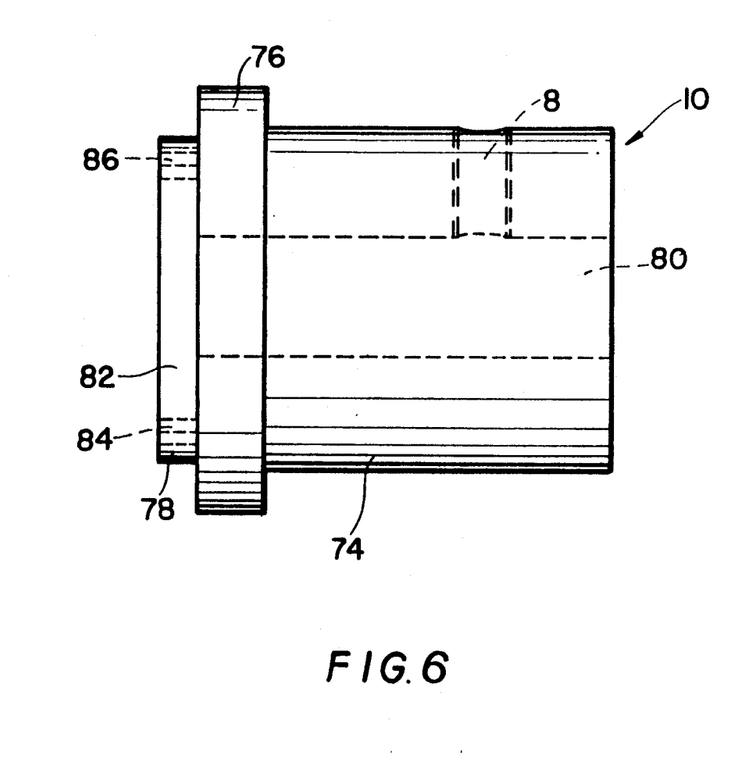
FIG. 6 shows a side view of the securing device for the chemical/physical sensor.
Figure 7:
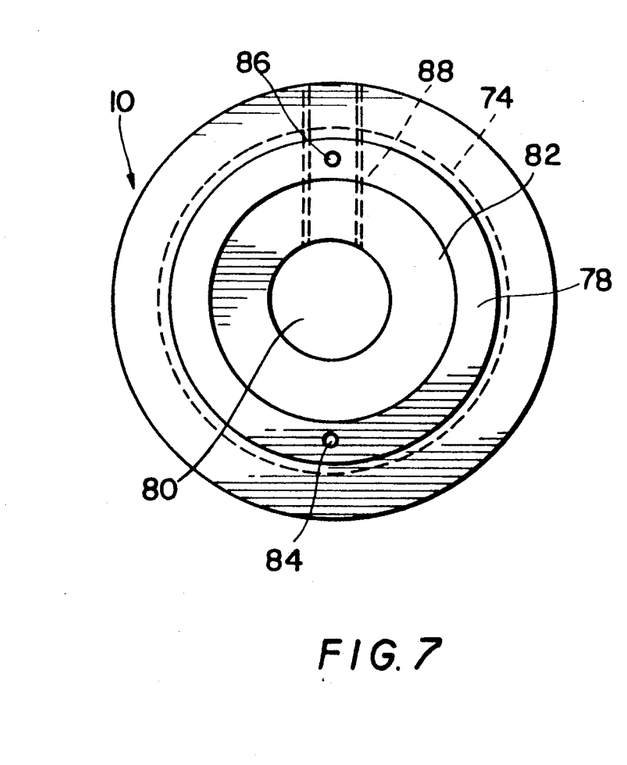
FIG. 7 shows a front view of the device shown in FIG. 6.

FIG. 6 and FIG. 7 shows a side view and front view of the securing device 10 for the chemical/physical sensor 4. The securing device 10 consists of a cylindrical body 74 which, in the area of the front end, widens into a cylindrical ring 76 which has a greater diameter and to the front side of which there is connected a cylindrical attachment 78 with a diameter corresponding approximately to the diameter of the recess 46. The cylindrical body 74 has a central bore 80. The bore 80 merges into a recess 82 in the attachment 78, in which respect the diameter of the attachment 78 corresponds to the diameter of the recess 44. Also provided in the attachment 78 are bores 84, 86 corresponding to the bores 48, 50 for receiving the fixing pins 72. Approximately in the middle area the cylindrical body 74 has a threaded radial bore 88 which extends outwards and which is provided for receiving and adjustment screw of VA steel 90. The adjustment screw 90 is provided for fixing an optical fibre bundle (not shown) which is introduced into the securing device 10 and which is intended as a signal line for the chemical/physical sensor 4.

Figure 8:
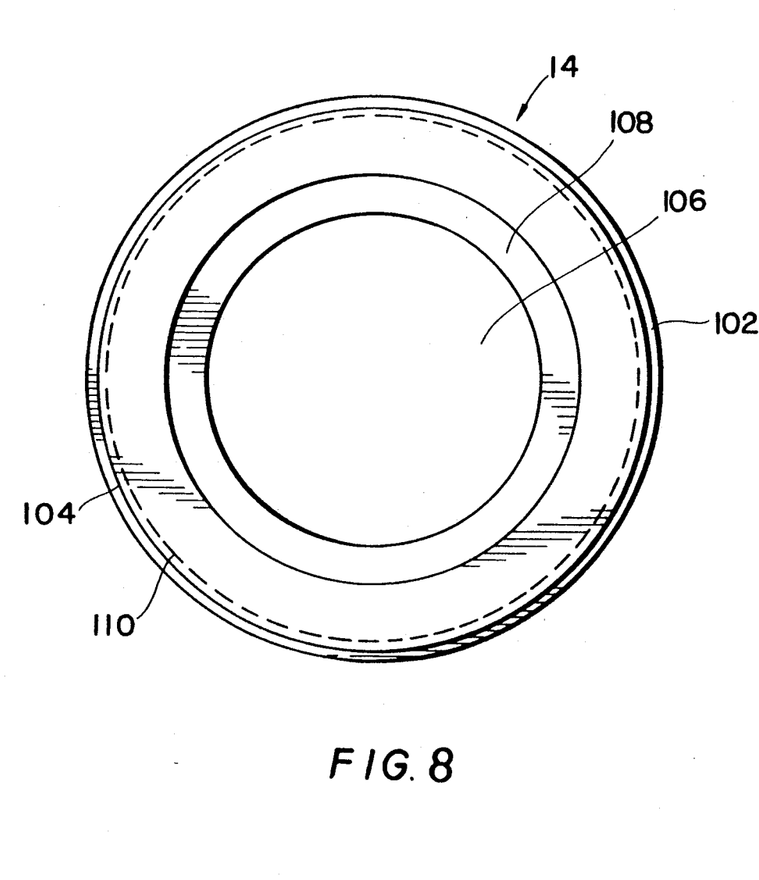
FIG. 8 shows a front view of the window securing device.
Figure 9:
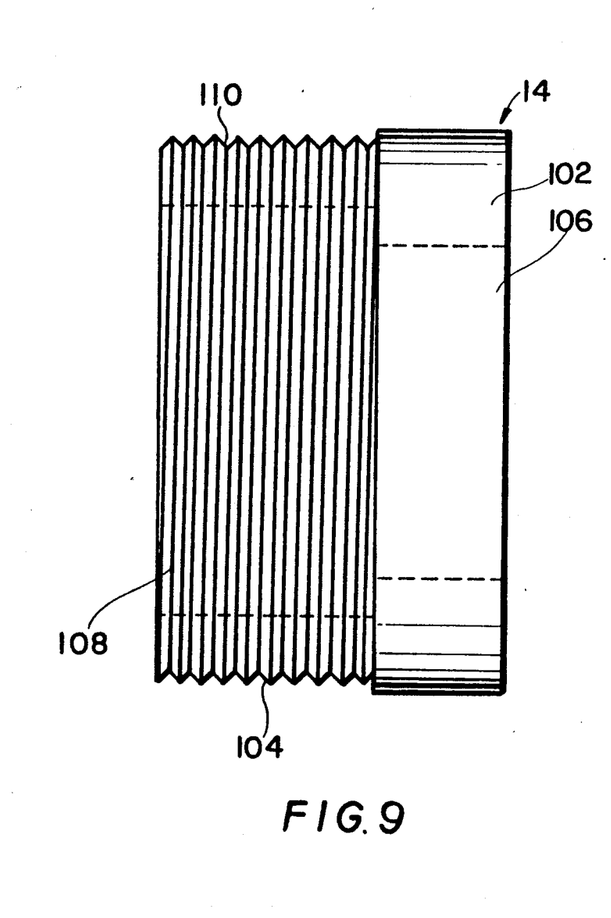
FIG. 9 shows a side view of the device shown in FIG. 8.

FIG. 8 and FIG. 9 show a front view and side view of the counter-screw 14, which at the same time has the function of a securing device for a window 100 to be described hereinbelow. The counter-screw 14 consists of a cylindrical ring 102 which merges into a cylindrical ring 104 of slightly smaller diameter. The former cylindrical ring 102 has a central bore 106 whose diameter corresponds to the external diameter of the cylindrical body 64, and the other cylindrical ring 014 has a central bore 108 whose internal diameter corresponds to the external diameter of the cylindrical ring 76. The cylindrical ring 104 moreover has an external thread 110 corresponding to the thread 66 of the annular body 60. By screwing together the union nut 12 and its counter-screw 14, the securing device 10 arranged in between and the flow chamber 6 are pressed together.

Figures 10, 11:
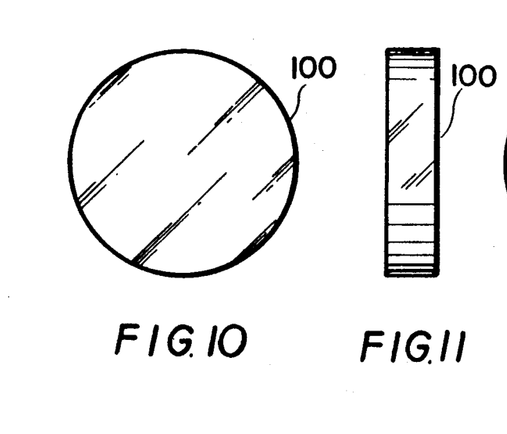
FIG. 10 is a partial front view of the window component of the arrangement of the invention.
FIG. 11 is a side view of the window of FIG. 10.
Figure 12:
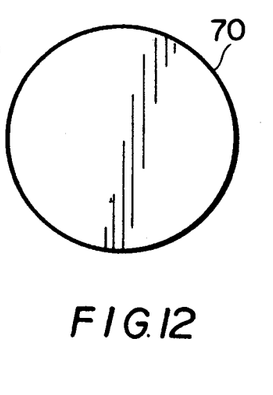
FIG. 12 is a front view of the optode used in the sensor component.
Figure 13:
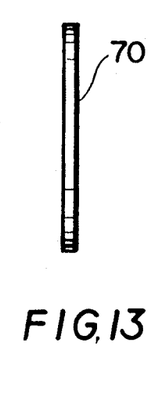
FIG. 13 is a side view of the optode shown in FIG. 12.

FIG. 10-19 shows individual representations of parts of the sensor arrangement. FIG. 11 and 12 shows the optical window 100 which, in the exemplary embodiment represented, is made of sapphire. The optode 70 lying on the optical window 100 is illustrated in FIG. 12 and FIG. 13 and is shown on a larger scale in FIG. 20. The optode 70 consists of a support film 92 which, in the exemplary embodiment shown, is a mylar film, i.e. a polyester film based on ethylene glycol and terephthalic acid. The support film 92 is provided with an indicator layer 94 of silicone and a fluorescence indicator contained therein. The optical signals emitted by the indicator layer 94 are transmitted through the optical window 100 to the optical fibre bundle.

Figure 14:
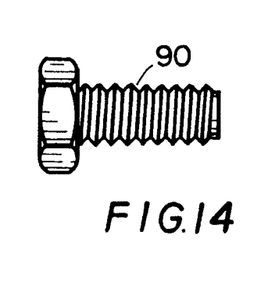
FIG. 14 is a side view of an adjustment screw for securing an optical fiber bundle used as optical receiver.
Figure 15:
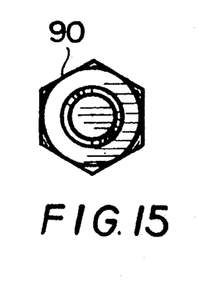
FIG. 15 is a top view of the screw shown in FIG. 14.
Figure 16:
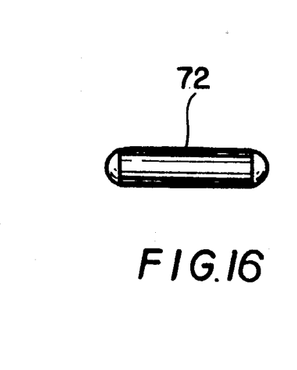
FIG. 16 is a side view of a fixing pin for securing against displacement of the transmitter in contact with the flow channel.
Figure 17:
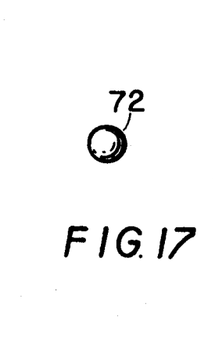
FIG. 17 is an end view of the pin shown in FIG. 16.

FIG. 14 and FIG. 15 illustrates the adjustment screw 90 for fixing the optical fibre bundle in the securing device 10. A cylindrical fixing pin 72, which is provided as an antidisplacement means for the optode 70, is illustrated in FIG. 16 and FIG. 17. The fixing pin 72 is received in the bores 48, 50.

Figures 18, 19:
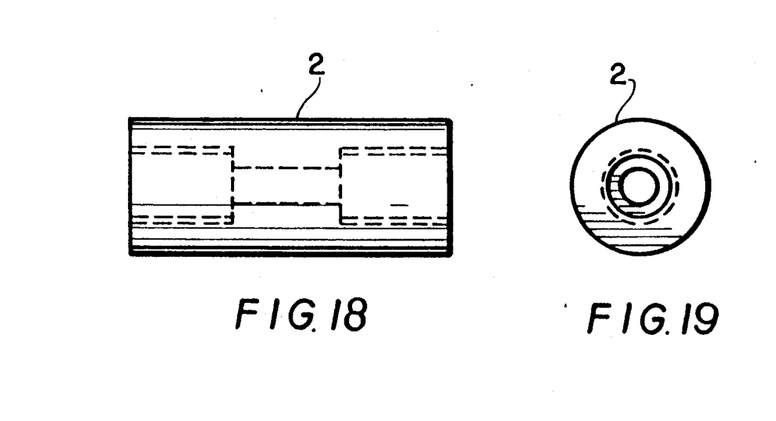
FIG. 18 is a side view of the enzyme reactor.
FIG. 19 is an end view of the enzyme reactor.
Figure 20:
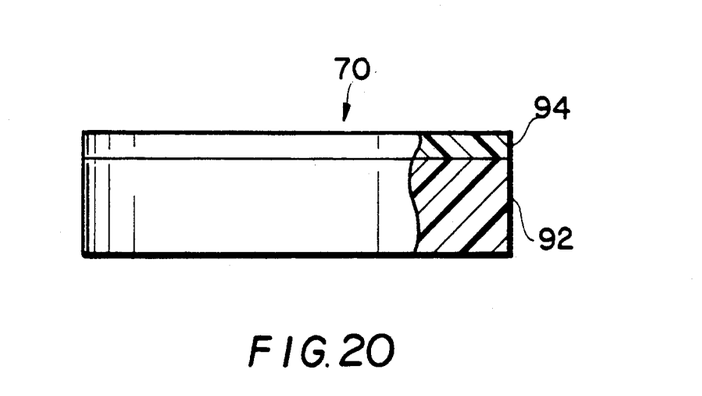
FIG. 20 shows a side view of the optode.

Finally, FIG. 18 and FIG. 19 shows the chemical/physical sensor.

We claim:

1. A sensor arrangement for flow injection analysis, which comprises;
   (a) a housing which is a sealed module;
   (b) a chemical/physical sensor contained within the housing and which comprises;
      (i) a transmitter constructed and arranged to emit optical signals;
      (ii) a receiver for said optical signals; and
      (iii) a window, transparent to the optical signals, positioned between the transmitter and the receiver;
   (c) an enzyme reactor mounted removably on the housing; and
   (d) a flow channel in open communication between the reactor and the sensor, said flow channel having a meander configuration within the housing, exceeding the distance between the reactor and the sensor.

2. The sensor arrangement of claim 1 wherein the housing is made of a material selected from the group consisting of poly(methyl) methacrylate and clear polyvinyl chloride.

3. The sensor arrangement of claim 1 wherein the enzyme reactor is an insert cartridge.

4. The sensor arrangement of claim 3 wherein the mounting on the housing comprises a screw fitting.

5. The sensor arrangement of claim 1 wherein the flow channel is in a flow chamber and is secured by a means for securing to the sensor.

6. The sensor arrangement of claim 5 wherein sid means for securing comprises a union nut and a counter-screw.

7. The sensor arrangement of claim 1 wherein the optical signal receiver is an optical fiber bundle.

8. The sensor arrangement of claim 1 wherein the window is fabricated from a material selected from the group consisting of sapphire and Quartz.

9. The sensor arrangement of claim 1 wherein the transmitter is an optode and consists of a support fiber and an indicator layer arranged on the support film.

10. The sensor arrangement of claim 9 wherein the support film is polyester, the reaction product of ethylene glycol and terephthalic acid and the indicator layer is a silicone containing a fluorescence indicator.

11. The sensor arrangement of claim 1 wherein the transmitter and the window are pressed together in a fluid-tight associated and an anti-displacement means is provided to maintain the association.

* * * * *